(12) United States Patent
Kankan et al.

(10) Patent No.: US 7,638,627 B2
(45) Date of Patent: Dec. 29, 2009

(54) PROCESS OF PREPARING IMATINIB AND IMATINIB PREPARED THEREBY

(75) Inventors: Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 429 days.

(21) Appl. No.: 10/546,193

(22) PCT Filed: Jan. 8, 2004

(86) PCT No.: PCT/GB2004/000018

§ 371 (c)(1),
(2), (4) Date: Oct. 31, 2005

(87) PCT Pub. No.: WO2004/074502

PCT Pub. Date: Sep. 2, 2004

(65) Prior Publication Data

US 2006/0173182 A1 Aug. 3, 2006

(30) Foreign Application Priority Data

Feb. 18, 2003 (GB) .................................. 0303730.6

(51) Int. Cl.
C07D 241/04 (2006.01)
C07D 295/00 (2006.01)
C07D 401/00 (2006.01)

(52) U.S. Cl. ...................................... 544/331; 544/390

(58) Field of Classification Search ................. 544/390, 544/331; 514/275
See application file for complete search history.

(56) References Cited

U.S. PATENT DOCUMENTS 5,521,184 A 5/1996 Zimmermann

FOREIGN PATENT DOCUMENTS

| EP | 564 409 | * | 3/1993 |
| EP | 0 564 409 A1 | | 10/1993 |
| WO | WO 99/03854 | * | 1/1999 |

OTHER PUBLICATIONS

Berge, et al., Pharmaceutical Salts, J. of Pharm. Sci., 66(1):1-19 (1977).*

International Preliminary Examination Report dated Sep. 1, 2005.
International Search Report dated Sep. 1, 2004.

* cited by examiner

Primary Examiner—James O Wilson
Assistant Examiner—Erich A Leeser
(74) Attorney, Agent, or Firm—Conley Rose, P.C.; Rodney B. Carroll

(57) ABSTRACT

A process of preparing imatinib, either as the free base or as an acid addition salt, which process comprises reacting N-(2-methyl-5-aminophenyl-4-(3-pyridyl)-2-pyrimidine amine of formula (II) with a 4-(4-methyl-piperazino methyl)benzoyl halide of formula (III) in the presence of an inert organic solvent, so as to yield a hydrohalide salt of imatinib formula (I) where n represents 1, 2 or 3 and Hal represents bromo, chloro, fluoro or iodo, either in anhydrous or hydrated form, which can as desired optionally be further converted either to the free base or a further acid addition salt. The present invention is also concerned with imatinib prepared according to the above process.

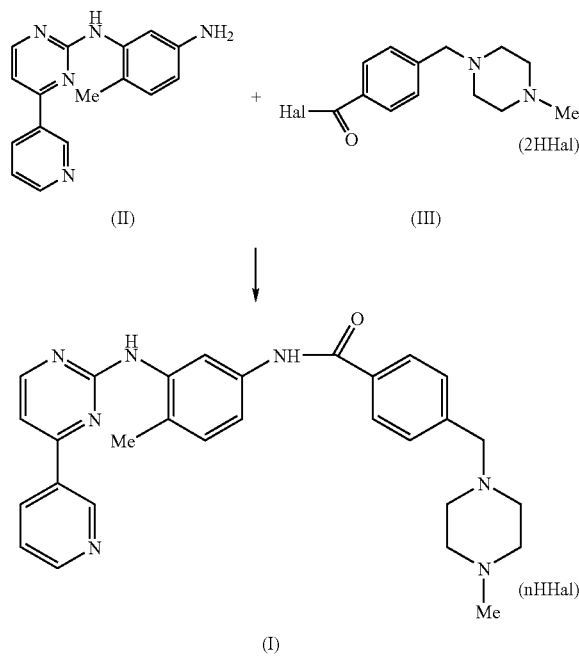

32 Claims, No Drawings

PROCESS OF PREPARING IMATINIB AND IMATINIB PREPARED THEREBY

This application is a 35 U.S.C. §371 U.S. National Stage Application of International Application No. PCT/GB2004/000018, filed on Jan. 8, 2004, claiming the priority of Great Britain Application No. 0303730.6, filed Feb. 18, 2003, the entire disclosures of which are incorporated herein by reference in their entireties.

The present invention is concerned with a process of preparing imatinib, either as the free base or as acid addition salts thereof, and also such imatinib free base and imatinib acid addition salts prepared by the process of the present invention.

Imatinib is the international non-proprietary name for N-{5-[4-(4-methyl piperazine methyl)-benzoylamido]-2-methylphenyl}-4-(3-pyridyl)-2-pyrimidine amine.

EP 0564409 describes the preparation of imatinib and the use thereof, especially as an anti-tumour agent. In particular, Example 21 describes the preparation of imatinib free base. There is no specific preparation of an imatinib salt in EP 0564409.

The synthesis of imatinib mesylate is described in WO 99/03854. WO 99/03854 describes preparation of imatinib mesylate from imatinib free base, the preparation of the latter being referred to above mentioned EP 0564409.

The prior art synthesis of imatinib in EP 0564409 involves reduction of (2-methyl-5-nitrophenyl-6-pyridin-3-yl-1,6-dihydro-pyrimidine-2-yl)amine of formula (IV) to yield N-(2-methyl-5-aminophenyl-4-(3-pyridyl)-2-pyrimidine amine of formula (II), followed by amidation involving N-(2-methyl-5-aminophenyl-4-(3-pyridyl)-2-pyrimidine amine of formula (II) with 4-(4-methyl-piperazino methyl)benzoyl chloride of formula (IIIa). In the prior art processes described in EP 0564409, the reduction reaction is usually carried out in presence of palladium catalyst under hydrogenation conditions. The condensation is carried out in presence of a base, such as pyridine, triethylamine or the like. The benzoyl chloride of formula (IIIa) is usually obtained as the dihydrochloride and used as such for the amidation step, and further an equivalent of hydrochloric acid is released during the reaction of N-(2-methyl-5-aminophenyl-4-(3-pyridyl)-2-pyrimidine amino of formula (II) with the benzoyl chloride of formula (IIIa). Hence, a person skilled in the art would be expected to use a base as a scavenger for the acid released during the reaction and also to neutralize the benzoyl chloride of formula (IIIa) prior to reaction with N-(2-methyl-5-aminophenyl-4-(3-pyridyl)-2-pyrimidine amine of formula (II).

We have found the above reaction as described in the above mentioned prior art to be unsatisfactory, whereby the reduction by hydrogenation involved large volumes of solvent, took long hours and gave a low yield (40-45%). The condensation reaction was also slow, gave rise to undesirable side products, and involved tedious work-up procedures. Use of a solvent such as pyridine in the last step was found to be undesirable, since it was difficult to remove residual traces thereof from the final product. Due to the additional purification steps required for removal of impurities in the process, the yield of the product was found to be low.

We have now found a surprisingly simple process for the preparation of imatinib, which process provides an improved reduction step of (2-methyl-5-nitrophenyl)-6-pyridin-3-yl-1,6-dihydro-pyrimidine-2-yl)-amine of formula (IV) to N-(2-methyl-5-aminophenyl-4-(3-pyridyl)-2-pyrimidine amine of formula (II) and an improved amidation step of N-(2-methyl-5-aminophenyl(3-pyridyl)-2-pyrimidine amine of formula (II) with a benzoyl halide of formula (III), which preparation overcomes the problems associated with the prior art method.

There is provided by the present invention, therefore, a process of preparing imatinib, either as the free base or as an acid addition salt, which process comprises reacting N-(2-methyl-5-aminophenyl-4-(3-pyridyl)-2-pyrimidine amine of formula (II) with a 4-(methyl-piperazino methyl)benzoyl halide of formula (III)

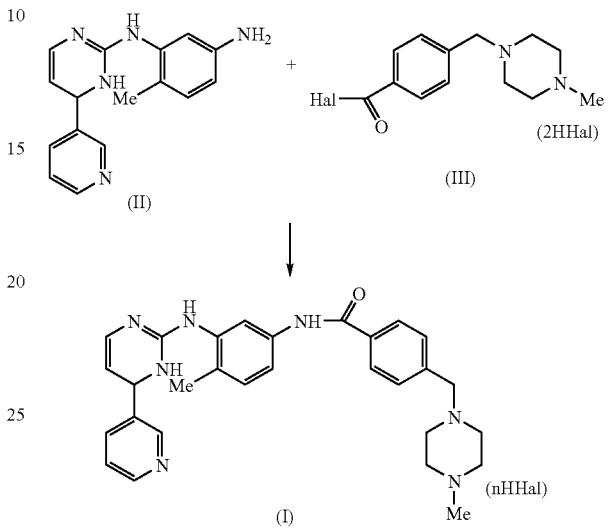

in the presence of an inert organic solvent, so as to yield a hydrohalide salt of imatinib of formula (I) where n represents 1, 2 or 3 and Hal represents bromo, chloro fluoro or iodo (in particular bromo or chloro, and especially chloro), either in anhydrous or hydrated form (in particular a hydrobromide or hydrochloride, and especially a hydrochloride), which can as desired optionally be further converted either to the free base or a further acid addition salt. A specific hydrochloride salt of imatinib of formula (I) prepared according to the present invention is imatinib trihydrochloride monohydrate.

In a preferred embodiment of the present invention, therefore, there is provided a process of preparing imatinib, either as the free base or as an acid addition salt, which process comprises reacting N-(2-methyl-5-aminophenyl-4-(3-pyridyl)-2-pyrimidine amine of formula (II) with 4-(4-methyl-piperazino methyl)benzoyl chloride of formula (IIIa)

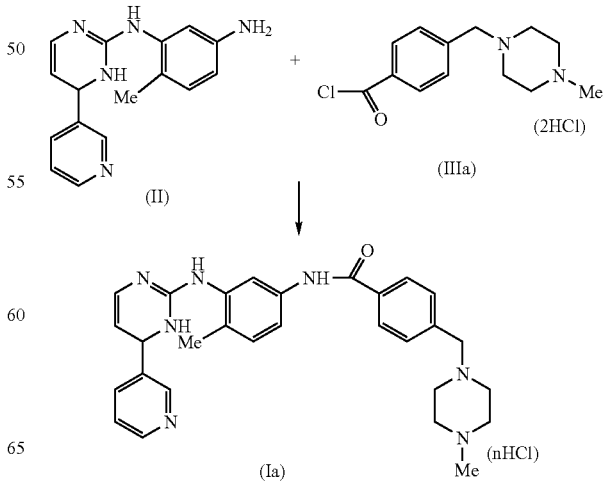

in the presence of an inert organic solvent, so as to yield an imatinib hydrohalide salt which is a hydrochloride salt of imatinib of formula (Ia) where n represents 1, 2 or 3, either in anhydrous or hydrated form, which can as desired optionally be further converted either to the free base or a further acid addition salt. A specific hydrochloride salt of imatinib of formula (Ia) prepared according to the present invention is imatinib trihydrochloride monohydrate.

There is also provided by the present invention a hydrohalide salt of imatinib of formula (I) either in anhydrous or hydrated form (I)

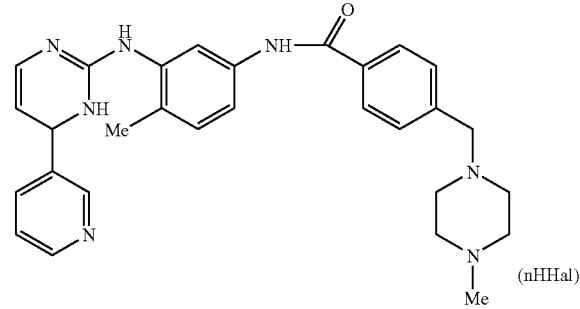

(nHHal)

where n represents 1, 2 or 3 and Hal represents bromo, chloro fluoro or iodo, in particular where the imatinib hydrohalide salt of formula (I) is a hydrobromide or hydrochloride salt of imatinib.

Particularly, the present invention provides a hydrochloride salt of imatinib of formula (Ia) either in anhydrous or hydrated form (Ia)

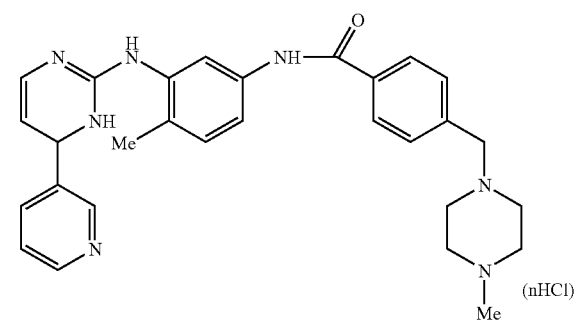

(nHCl)

where n represents 1, 2 or 3.

A specific hydrochloride salt of imatinib prepared according to the present invention is imatinib trihydrochloride monohydrate.

The present invention also provides a hydrohalide salt of imatinib of formula (I) either in anhydrous or hydrated form obtained by a process substantially as hereinbefore described (I)

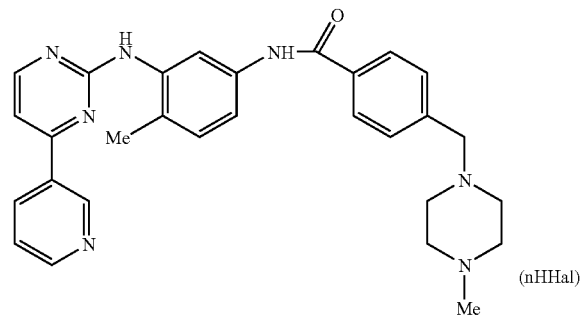

(nHHal)

where n represents 1, 2 or 3 and Hal represents bromo, chloro fluoro or iodo, in particular where the imatinib hydrohalide salt of formula (I) is a hydrobromide or hydrochloride salt of imatinib.

Particularly, the present invention provides a hydrochloride salt of imatinib of formula (Ia) either in anhydrous or hydrated form (especially imatinib trihydrochloride monohydrate) obtained by a process substantially as hereinbefore described (Ia)

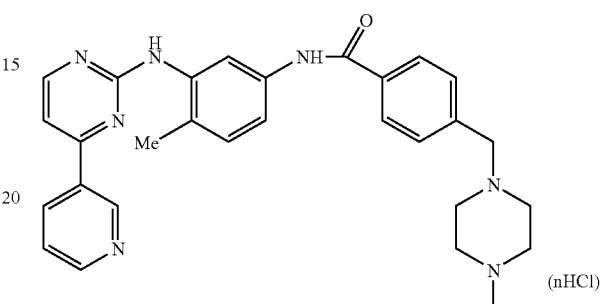

(nHCl)

where n represents 1, 2 or 3.

Suitably a hydrohalide salt of imatinib of formula (I), in particular a hydrobromide or hydrochloride salt of imatinib, and especially a hydrochloride salt of imatinib of formula (Ia), substantially as hereinbefore described can be employed as an intermediate in the preparation of imatinib free base or a further acid addition salt of imatinib, such as imatinib mesylate substantially as hereinafter described in greater detail.

By "inert organic solvent" is meant an organic solvent, which under the reaction conditions of a process according to the present invention, does not enter into any appreciable reaction with either the reactants or the products. A suitable inert organic solvent for use in a process according to the present invention can be selected from the group consisting of dimethylformamide, dimethyl acetamide, N-methylpyrrolidone, sulfolane, diglyme dioxane, tetrahydrofuran and other inert organic solvents known in the art. A particularly suitable inert organic solvent for use in the above process according to the present invention is dimethylformamide.

It will be appreciated from the above that the above process step does not employ a scavenger base for the reaction as is taught by the prior art, but is carried out under mild conditions whereby very little by-products are produced in the reaction. The work-up of the above process step is very easy and the product is filtered from the reaction mass as a hydrohalide salt of formula (I). The isolation of imatinib as a hydrohalide salt is a method of purification of the product. Furthermore, the above process is suitable for large-scale production and is economical to operate.

In the case where a hydrohalide salt of imatinib of formula (I), especially a hydrochloride salt of imatinib of formula (Ia), is converted to imatinib free base employing a process according to the present invention, suitably the imatinib hydrohalide salt of formula (I) can be treated with a suitable base so as to yield imatinib free base. A process according to the present invention may further comprise converting a hydrohalide salt of imatinib of formula (I), especially a hydrochloride salt of imatinib of formula (Ia), to a further acid addition salt of imatinib suitably by treatment of imatinib free base prepared as above, with an appropriate amount of an acid. Preferably methane sulphonic acid is employed so as to yield imatinib mesylate by a process according to the present invention.

In a preferred aspect of the present invention, there is provided a process of preparing imatinib free base, which process comprises reacting N-(2-methyl-5-aminophenyl-4-(3-pyridyl)-2-pyrimidine amine of formula (II) with a 4 (methyl-piperazino methyl)benzoyl halide of formula (III)

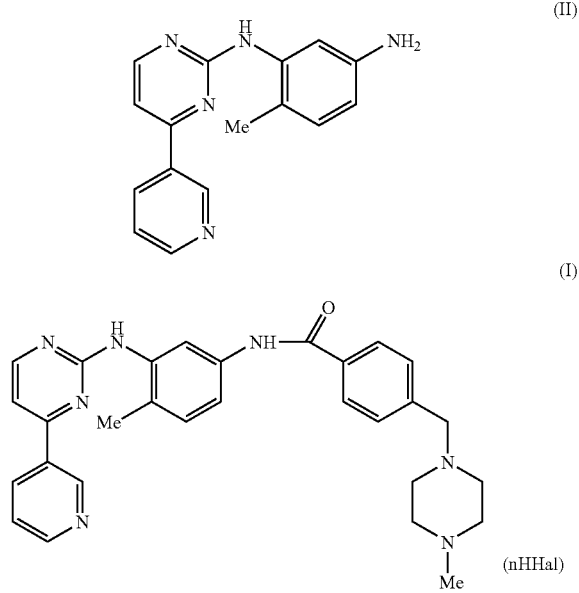

(II)

(I)

(nHHal)

in the presence of an inert organic solvent, so as to yield a hydrohalide salt of imatinib of formula (I) where n represents 1, 2 or 3 and Hal represents bromo, chloro fluoro or iodo (in particular bromo or chloro, and especially chloro), either in anhydrous or hydrated form (in particular a hydrobromide or hydrochloride, and especially a hydrochloride, typically imatinib trihydrochloride monohydrate), and further converting the resulting hydrohalide salt of imatinib of formula (I) to imatinib free base. Typically the conversion comprises treatment of the imatinib hydrohalide salt of formula (I) with a suitable base so as to yield imatinib free base substantially as hereinbefore described.

In a preferred aspect of the present invention, there is provided a process of preparing imatinib free base, which process comprises reacting N-(2-methyl-5-aminophenyl-4-(3-pyridyl)-2-pyrimidine amine of formula (II) with methyl-piperazino methyl)benzoyl chloride of formula (III)

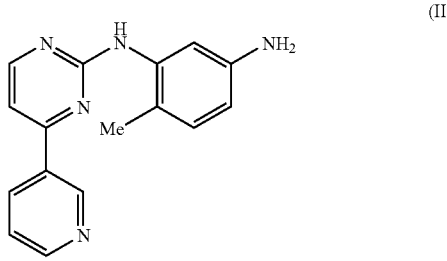

(II)

-continued

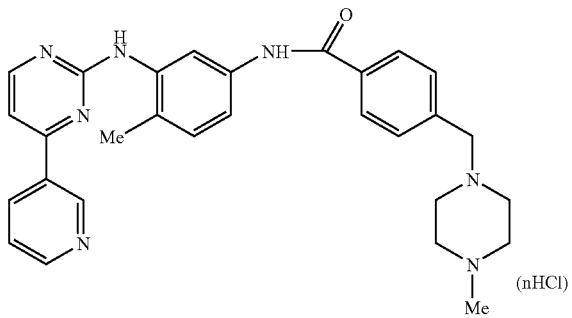

(Ia)

(nHCl)

in the presence of an inert organic solvent, so as to yield an imatinib hydrohalide salt which is a hydrochloride salt of imatinib of formula (Ia) where n represents 1, 2 or 3, either in anhydrous or hydrated form (typically imatinib trihydrochloride monohydrate), and further converting the resulting hydrochloride salt of imatinib of formula (Ia) to imatinib free base. Typically the conversion comprises treatment of the imatinib hydrochloride of formula (Ia) with a suitable base so as to yield imatinib free base substantially as hereinbefore described.

There is, therefore, further provided by the present invention imatinib free base obtained by a process according to the present invention substantially as hereinbefore described.

The present invention also provides a process of preparing an acid addition salt of imatinib, which process comprises reacting N-(2-methyl-5-aminophenyl-4-(3-pyridyl)-2-pyrimidine amine of formula (II) with a 4-(4-methyl-piperazino methyl)benzoyl halide of formula (III)

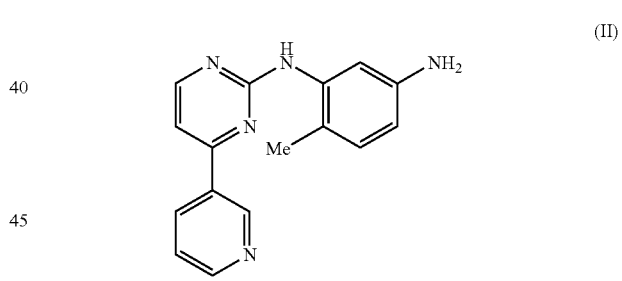

(II)

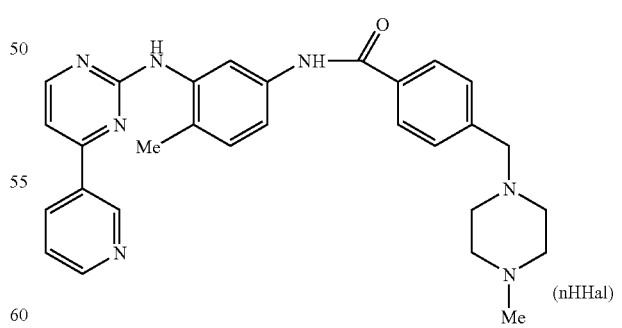

(I)

(nHHal)

in the presence of an inert organic solvent, so as to yield a hydrohalide salt of imatinib of formula (I) where n represents 1, 2 or 3 and Hal represents bromo, chloro fluoro or iodo (in particular bromo or chloro, and especially chloro), either in anhydrous or hydrated form (in particular a hydrobromide or hydrochloride, and especially a hydrochloride, typically imatinib trihydrochloride monohydrate), which is further converted to a further acid addition salt. Typically the conversion comprises treating a hydrohalide salt of imatinib of formula (I) either in anhydrous or hydrated form (in particular a hydrobromide or hydrochloride, and especially a hydrochloride), with a suitable base so as to yield imatinib free base substantially as hereinbefore described and subsequently treating imatinib free base with a further acid (typically methane sulphonic acid) so as to yield a further acid addition salt of imatinib (typically imatinib mesylate).

Preferably, the present invention provides a process of preparing an acid addition salt of imatinib, which process comprises reacting N-(2-methyl-5-aminophenyl-4-(3-pyridyl)-2-pyrimidine amine of formula (II) with 4-(4-methylpiperazino methyl)benzoyl chloride of formula (IIIa)

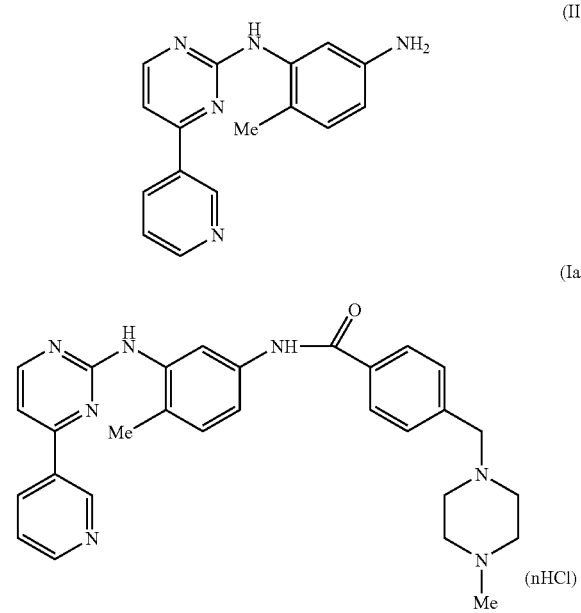

in the presence of an inert organic solvent, so as to yield an imatinib hydrohalide salt which is a hydrochloride salt of imatinib of formula (Ia) where n represents 1, 2 or 3, either in anhydrous or hydrated form (typically imatinib trihydrochloride monohydrate), which is further converted to a further acid addition salt. Typically the conversion comprises treating a hydrochloride salt of imatinib of formula (Ia) with a suitable base so as to yield imatinib free base substantially as hereinbefore described and subsequently treating imatinib free base with a further acid (typically methane sulphonic acid) so as to yield a flirter acid addition salt of imatinib (typically imatinib mesylate).

The present invention further provides an acid addition salt of imatinib prepared by a process according to the present invention substantially as hereinbefore described. The acid addition salt provided by the present invention can be an imatinib hydrochloride salt of formula (Ia) either in anhydrous or hydrated form substantially as hereinbefore described (typically imatinib trihydrochloride monohydrate), or imatinib mesylate suitably obtained from an imatinib hydrochloride salt of formula (Ia) either in anhydrous or hydrated form via imatinib free base again substantially as hereinbefore described.

A process according to the present invention preferably fibber comprises preparation of N-(2-methyl-5-aminophenyl-4-(3-pyridyl)-2-pyrimidine amine of formula (II) from (2-methyl-5-nitrophenyl)-6-pyrin 3-yl-1,6-dihydro-pyrimidine-2-yl)-amine of formula (I)

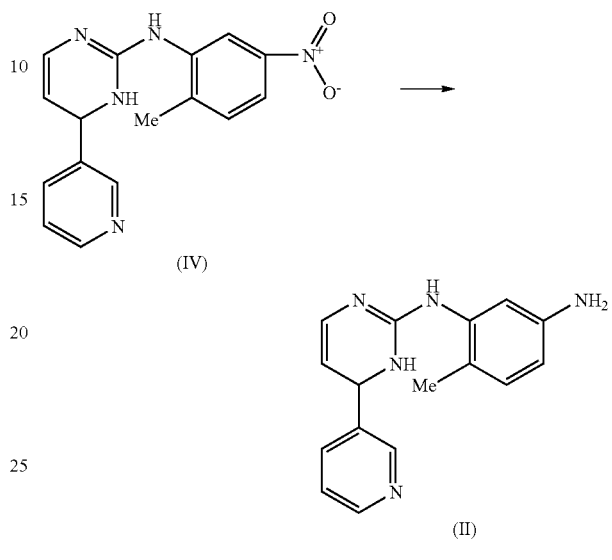

which process is carried out in the presence of a chemical reducing agent suitably in acidic solution, or more particularly where the chemical reducing agent comprises a metal or metal salt, and where a particularly preferred process according to the present invention is carried out in the presence of stannous chloride and hydrochloride acid.

It will be appreciated that a process according to the present invention does not employ hydrogenation, but a chemical reduction process preferably with stannous chloride, which results in improved yields (65-70%), less use of solvents and improved purity.

A process according to the present invention can suitably be illustrated as follows:

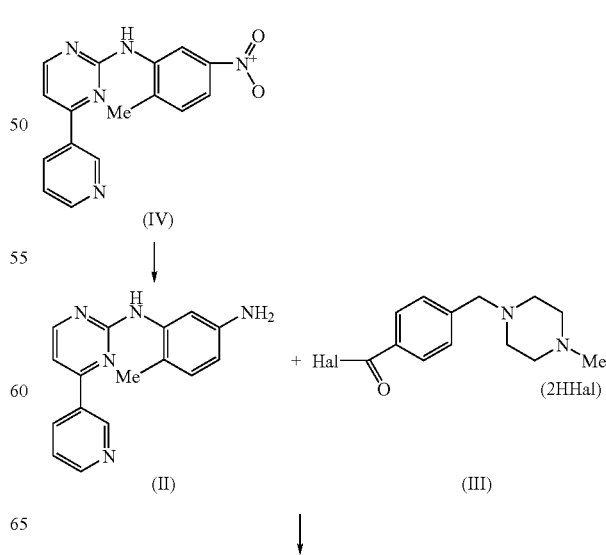

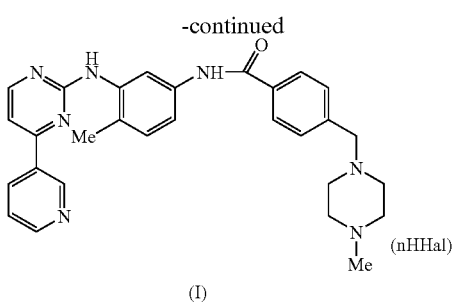

wherein the reduction of (2-methyl-5-nitrophenyl)-6-pyridin-3-yl-1,6-dihydro-pyrimidine-2-yl)-amine of formula (IV) to yield N-(2-methyl-5-aminophenyl-4-(3-pyridyl)-2-pyrimidine amine of formula (II) is carried out in the presence of a chemical reducing agent and the reaction of N-(2-methyl-5-aminophenyl-3-pyridyl)-2-pyrimidine amine of formula (II) with a 4-(4-methyl-piperazino methyl)benzoyl halide of formula (II) is carried out in the presence of an inert organic solvent, so as to yield a hydrohalide salt of imatinib of formula (I) where n and Hal are substantially as hereinbefore described, either in anhydrous or hydrated form, which can as desired optionally be further converted either to the free base or a further acid addition salt substantially as hereinbefore described.

A preferred such process according to the present invention can be as follows:

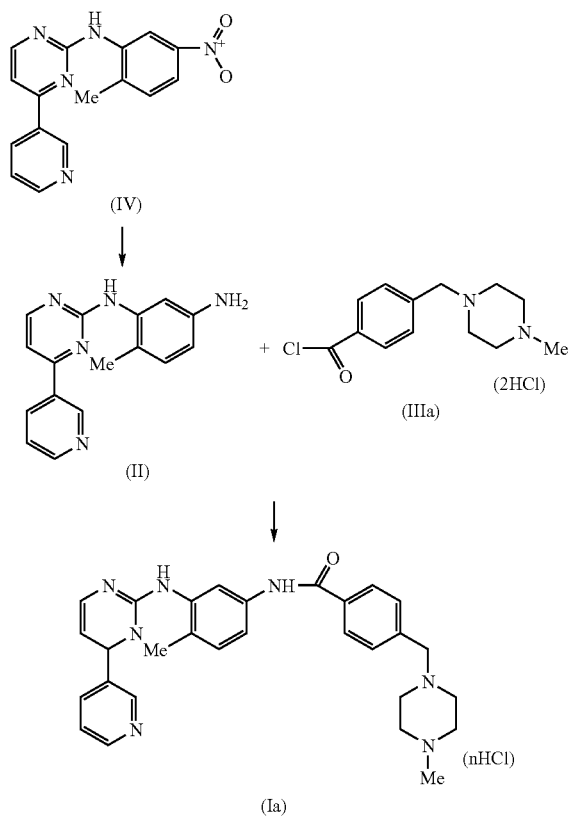

wherein the reduction of (2-methyl-5-nitrophenyl)-6-pyridin-3-yl-1,6-dihydro-pyrimidine-2-yl)-amine of formula (IV) to yield N-(2-methyl-5-aminophenyl-4-(3-pyridyl)-2-pyrimidine amine of formula (II) is carried out in the presence of a chemical reducing agent and the reaction of N-(2-methyl-5-aminophenyl-3-pyridyl)-2-pyrimidine amine of formula (II) with 4-(4-methyl-piperazino methyl)benzoyl chloride of formula (IIIa) is carried out in the presence of an inert organic solvent, so as to yield a hydrochloride salt of imatinib of formula (Ia) where n is substantially as hereinbefore described either in anhydrous or hydrated form, which can as desired optionally be ether converted either to the free base or a further acid addition salt substantially as hereinbefore described.

Imatinib, either as the free base or as an acid addition salt, according to the present invention, is particularly suitable for use as an antineoplastic as described in further detail in prior art document WO99/03854. There is further provided by the present invention, therefore, a pharmaceutically acceptable composition comprising an effective amount of imatinib substantially as hereinbefore described, together with a pharmaceutically acceptable carrier, diluent or excipient therefor.

The term "effective amount" as used herein means an amount of imatinib which is capable of preventing, ameliorating or eliminating a disease state, in particular tumour disease, for which administration of an antineoplastic is indicated. Typically imatinib is employed so as exhibit anti-proliferative and especially tumour inhibiting efficacy.

By "pharmaceutically acceptable composition" is meant that the carrier, diluent or excipient must be compatible with imatinib and not be deleterious to a recipient thereof. Suitable pharmaceutically acceptable compositions according to the present invention can be those suitable for topical, enteral, for example oral or rectal, or parenteral administration and may be solid or liquid. Especially tablets or gelatin capsules containing imatinib substantially as hereinbefore described together with adjuvants or diluents, can be used for oral administration. Solutions for injection may also be prepared according to the present invention by dissolving imatinib substantially as hereinbefore described in a solvent for injection and suitable additives conventionally used in the art may also be added.

It is also known from WO99/03854 that imatinib mesylate can prevent the development of multidrug resistance in cancer therapy with other antitumour agents or abolishes a pre-existing resistance to other antitumour agents. There is also provided by the present invention, therefore, a product containing imatinib, either as the free base or an acid addition salt substantially as hereinbefore described, and a further antitumour agent, for simultaneous, separate or sequential use in the treatment of tumour disease.

The present invention further provides imatinib, either as the free base or an acid addition salt substantially as hereinbefore described, for use in the manufacture of a medicament for the treatment of a disease state prevented, ameliorated or eliminated by the administration of an antineoplastic.

The present invention also provides a method of treating a disease state prevented, ameliorated or eliminated by the administration of an antineoplastic in an animal patient in need of such treatment, in particular tumour disease, which process comprises administering to the patient an effective amount of imatinib substantially as before described. In particular such methods according to the present invention can comprise use of imatinib for treatment of tumours, such as gliomas, ovarian tumours, prostate tumours, colon tumours and tumours of the Lung, such as especially small cell lung carcinoma and tumours of the breast or other gynaecological tumours. Depending on the species, age, individual condition, mode of administration and the clinical picture in question, effective doses, for example daily doses of about 1-2500 mg, typically 1-1000 mg, more typically 5-500 mg, can be administered.

The present invention will now be further illustrated by reference to the following Intermediates and Examples, which do not limit the scope of the invention in any way.

Intermediates

Preparation of (2-methyl-5-aminophenyl)-6-(pyridin-3-yl-1,6-dihydro-pyrimidine-2-yl)-amine (2-methyl-5-nitrophenyl-6-(pyridin-3-yl-1,6-dihydro-pyrimidine-2-yl)-amine (25 gms) was dissolved in tetrahydrofuran (250 ml). To this stannous chloride (90 gms) was added and heated to 60° C. for 4 hours. The reaction was cooled and filtered. The solids were dissolved in water, basified and extracted in ethylacetate. The organic layer was concentrated to give the title compound as a yellow colored solid.

Preparation of (2-methyl-5-aminophenyl)-6-(pyridin-3-yl-1,6-dihydro-pyrimidine-2-yl)-amine (2-methyl-5-nitrophenyl)-6-(pyridin-3-yl-1,6-dihydropyrimidine-2-yl)-amine (25 gms) was suspended in water (200 ml) and 200 ml of concentrated hydrochloric acid. To this stannous chloride (75 gms) was added and heated to 50° C. for 2 hours. The reaction was cooled and neutralized with sodium hydroxide. The solids were filtered. The solids were extracted with ethyl acetate. The organic layer was concentrated to give the title compound as a yellow colored solid.

EXAMPLES

Example 1

Preparation of N-{5-[4-(4-methyl piperazine methyl)-benzoylamido]-2-methylphenyl}-4-(3-pyridyl)-2-pyrimidine amine hydrochloride (Imatinib trihydrochloride monohydrate)

N-(2-methyl-5-aminophenyl-4-(3-pyridyl)-2-pyrimidine amine 5.0 g was suspended in dimethyl formamide (25 ml). To his was added under stirring, 4-(methyl-piperazino methyl)benzoyl chloride dihydrochloride (7.5 gms). The reaction mixture was heated under nitrogen for 15 hours at 70° C. After completion of the reaction, the reaction mixture was cooled to 20° C., stirred for 2 hours and filtered. The product obtained was dried under vacuum at 60° C. for 6 hours to give the title compound (6 gms), as a pale yellow solid.

Example 2

N-{5-[4-(methylpiperazinemethyl)-benzoylamido]-2-methylphenyl}-4-(3-pyridyl)-2-pyrimidine amine free base (Imatinib free base)

N-{5-[4-(4-methyl piperazine methyl)-benzoylamido]-2-methylphenyl}-4-(3-pyridyl)-2-pyrimidine amine trihydrochloride (25 gms) as prepared by Example 1 was dissolved in 100 ml of water, treated with charcoal and filtered. The pH of the clear filtrate was adjusted to about 10 with aq. ammonia. The precipitated solids were filtered and dried under vacuum to give the title compound.

Example 3

N-{5-[4-(4-methyl piperazine methyl)-benzoylamino]-2-methylphenyl}-4-(3-pyridyl-2-pyrimidine amine mesylate (Imatinib mesylate)

N-{5-[4-(4-methyl piperazine methyl)-benzoylamido]-2-methylphenyl}-4-(3-pyridyl)-2-pyrimidine amine free base (50 gms) was suspended in isopropanol (500 ml). Methane sulphonic acid (9.85 gms) was added and the reaction mixture was refluxed for 2 hours. The reaction mixture was concentrated to about 100 ml volume, cooled and the product isolated to the title compound as the mesylate salt. (55 gms).

The invention claimed is:

1. A process of preparing imatinib, either as the free base or as an acid addition salt, which process comprises reacting N-(2-methyl-5-aminophenyl-4-(3-pyridyl)-2-pyrimidine amine of formula (II) with a 4-(4-methyl-piperazino methyl) benzoyl halide of formula (III)

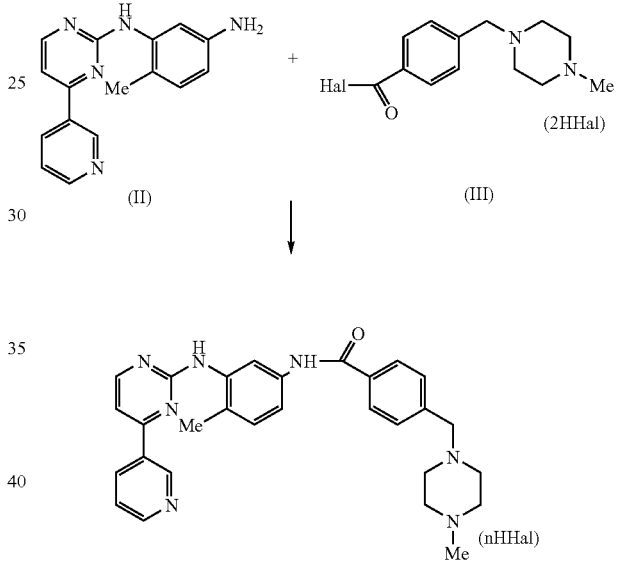

in the presence of an inert organic solvent, so as to yield a hydrohalide salt of imatinib of formula (I) where n represents 1, 2 or 3 and Hal represents bromo, chloro, fluoro or iodo, either in anhydrous or hydrated form which can as desired optionally be further converted either to the free base or a further acid addition salt.

2. The process according to claim 1, wherein Hal represents bromo or chloro, and whereby the imatinib hydrohalide salt prepared is a hydrobromide or hydrochloride salt of imatinib.

3. The process according to claim 2, wherein Hal represents chloro, and whereby the imatinib hydrohalide salt prepared is a hydrochloride salt of imatinib.

4. The process according to claim 3, wherein the imatinib hydrohalide salt prepared is imatinib trihydrochloride monohydrate.

5. A process of preparing imatinib, either as the free base or as an acid addition salt, which process comprises reacting N-(2-methyl-5-aminophenyl-4-(3-pyridyl)-2-pyrimidine amine of formula (II) with 4-(4-methyl-piperazino methyl) benzoyl chloride of formula (IIIa)

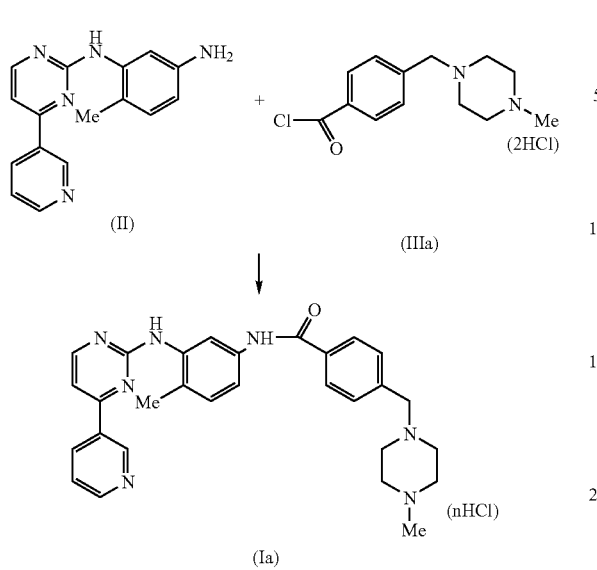

in the presence of an inert organic solvent, so as to yield an imatinib hydrohalide salt which is a hydrochloride salt of imatinib of formula (Ia) where n represents 1, 2 or 3, either in anhydrous or hydrated form, which can as desired optionally be further converted either to the free base or a further acid addition salt.

6. The process according to claim 5, wherein the imatinib hydrohalide salt prepared is imatinib trihydrochloride monohydrate.

7. The process according to claim 1, wherein said inert organic solvent is selected from the group consisting of dimethylformamide, dimethyl acetamide, N-methyl pyrrolidone, sulfolane, diglyme dioxane and tetrahydrofuran.

8. The process according to claim 7, wherein said inert organic solvent comprises dimethylformamide.

9. The process according to claim 1, wherein the imatinib hydrohalide salt is treated with a base so as to yield imatinib free base.

10. The process according to claim 9, wherein said imatinib free base is treated with an acid so as to yield a further acid addition salt of imatinib.

11. The process according to claim 10, wherein said imatinib free base is treated with methane sulfonic acid so as to yield imatinib mesylate.

12. A process of preparing imatinib free base, which process comprises reacting N-(2-methyl-5-aminophenyl-4-(3-pyridyl)-2-pyrimidine amine of formula (II) with a methyl-piperazino methyl)benzoyl halide of formula (III)

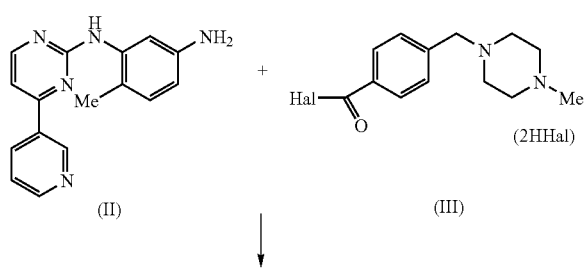

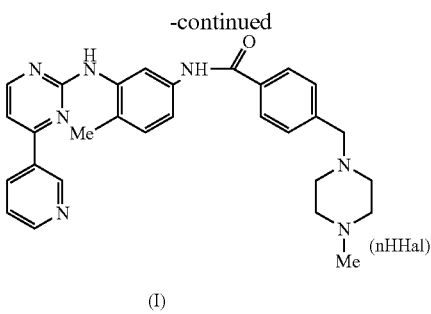

in the presence of an inert organic salt, so as to yield a hydrohalide salt of imatinib of formula (I) where n represents 1, 2, or 3 and Hal represents bromo, chloro, fluoro, or iodo, either in anhydrous or hydrated form and further converting the resulting hydrohalide salt of imatinib to imatinib free base.

13. The process according to claim 12, wherein Hal represents bromo or chloro, and whereby the imatinib hydrohalide salt prepared is a hydrobromide or hydrochloride salt of imatinib.

14. The process according to claim 13, wherein Hal represents chloro, and whereby the imatinib hydrohalide salt prepared is a hydrochloride salt of imatinib.

15. The process according to claim 14, wherein the imatinib hydrohydrate salt prepared is imatinib trihydrochloride monohydrate.

16. A process of preparing imatinib free base, which process comprises reacting N-(2-methyl-5-aminophenyl-4-(3-pyridyl)-2-pyrimidine amine of formula (II) with 4-(4-methylpiperazino methyl)benzoyl chloride of formula (IIIa)

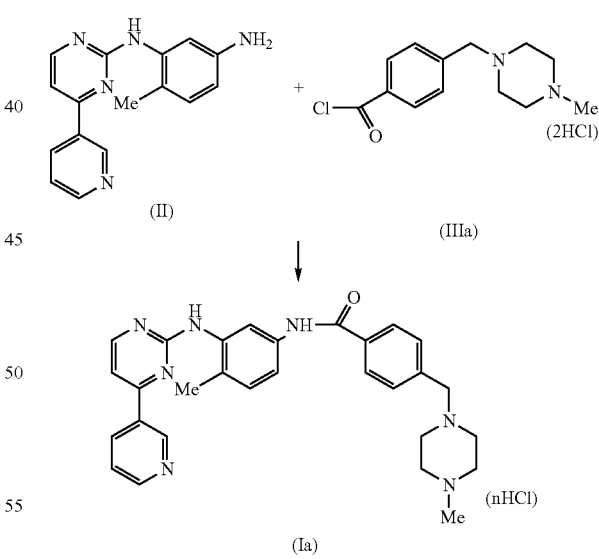

in the presence of an inert organic solvent, so as to yield a hydrochloride salt of imatinib of formula (Ia) where n represents 1, 2, or 3, and further converting the resulting hydrochloride salt of imatinib to imatinib free base.

17. The process according to claim 12, which comprises treating the imatinib hydrohalide salt prepared with a base so as to yield imatinib free base.

18. A process of preparing an acid addition salt of imatinib, which process comprises reacting N-(2-methyl-5-aminophenyl-4-(3-pyridyl)-2-pyrimidine amine of formula (II) with a 4-(4-methyl-piperazino methyl)benzoyl halide of formula (III)

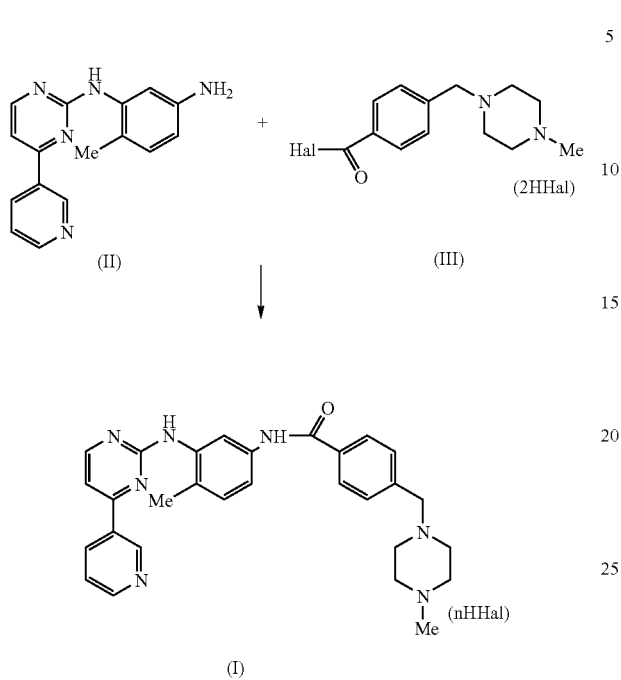

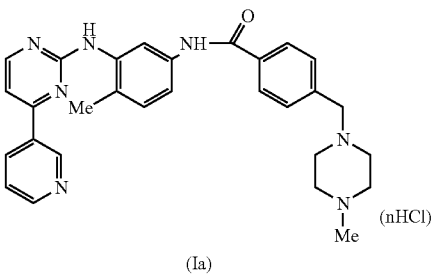

(Ia)

in the presence of an inert organic solvent, so as to yield an imatinib hydrohalide salt which is a hydrochloride salt of imatinib of formula (Ia) where n represents 1, 2 or 3 either in anhydrous or hydrated form, which is further converted to a further acid addition salt.

23. The process according to claim 22, which comprises treating the imatinib hydrohalide salt with a base so as to yield imatinib free base and subsequently treating imatinib free base with an acid.

24. The process according to claim 20, which comprises treating imatinib free base with methane sulfonic acid so as to yield imatinib mesylate.

in the presence of an inert organic solvent, so as to yield a hydrohalide salt of imatinib of formula (I) where n represents 1, 2 or 3 and Hal represents bromo, chloro, fluoro, or iodo, either in anhydrous or hydrated form which is further converted to a further acid addition salt.

19. The process according to claim 18, wherein Hal represents bromo or chloro, and whereby the imatinib hydrohalide salt prepared is a hydrobromide or hydrochloride salt of imatinib.

20. The process according to claim 19, wherein Hal represents chloro, and whereby the imatinib hydrohalide salt prepared is a hydrochloride salt of imatinib.

21. The process according to claim 20, wherein the imatinib hydrohalide salt prepared is imatinib trihydrochloride monohydrate.

22. A process of preparing an acid addition salt of imatinib, which process comprises reacting N-(2-methyl-5-aminophenyl-4-(3-pyridyl)-2-pyrimidine amine of formula (II) with 4-(4-methyl-piperazino methyl)benzoyl chloride of formula (IIIa)

25. The process according to claim 1, which further comprises preparing N-(2-methyl-5-aminophenyl-4-(3-pyridyl)-2-pyrimidine amine of formula (II) from (2-methyl-5-nitrophenyl)-6-pyridin-3-yl-1,6-dihydro-pyrimidine-2-yl)-amine of formula (IV)

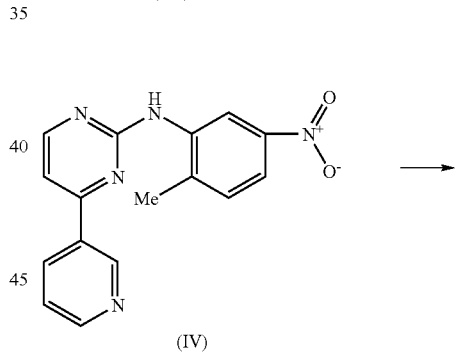

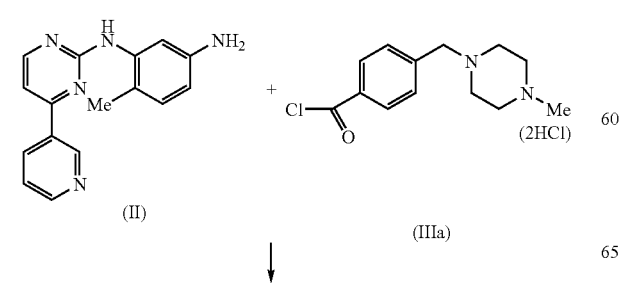

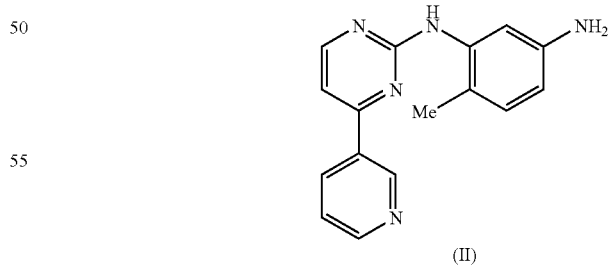

which process is carried out in the presence of a chemical reducing agent.

26. The process according to claim 25, wherein the chemical reducing agent comprises a metal or metal salt.

27. The process according to claim 26, which is carried out in the presence of stannous chloride and hydrochloride acid.

28. A process illustrated by the following scheme:

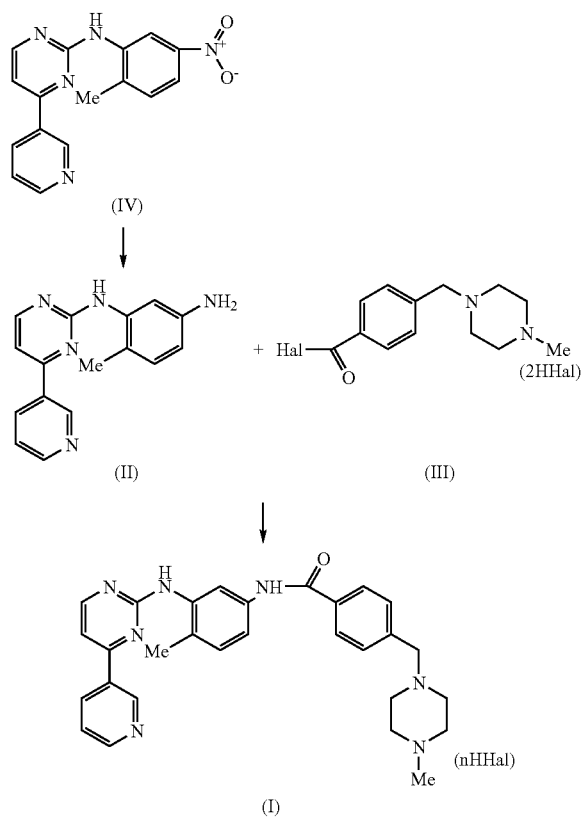

wherein the reduction of (2-methyl-5-nitrophenyl)-6-pyridin-3-yl-1,6-dihydro-pyrimidine-2-yl)-amine of formula (IV) to yield N-(2-methyl-5-aminophenyl-4-(3-pyridyl)-2-pyrimidine amine of formula (II) is carried out in the presence of a chemical reducing agent and the reaction of N-(2-methyl-5-aminophenyl-4-(3-pyridyl)-2-pyrimidine amine of formula (II) with a 4-(4-methyl-piperazino methyl)benzoyl halide of formula (III) is carried out in the presence of an inert organic solvent, so as to yield a hydrohalide salt of imatinib of formula (I) where n represents 1, 2 or 3 and Hal represents bromo, chloro, fluoro, or iodo, either in anhydrous or hydrated form, which can as desired optionally be further converted either to the free base or a further acid addition salt.

29. The process according to claim 28, wherein Hal represents bromo, or chloro and whereby the imatinib hydrohalide salt prepared is a hydrobromide or hydrochloride salt of imatinib.

30. A process according to claim 29, wherein Hal represents chloro and whereby the imatinib hydrohalide salt prepared is a hydrochloride salt of imatinib.

31. The process according to claim 30, whereby the imatinib hydrohalide salt prepared is imatinib trihydrochloride monohydrate.

32. A process illustrated by the following scheme:

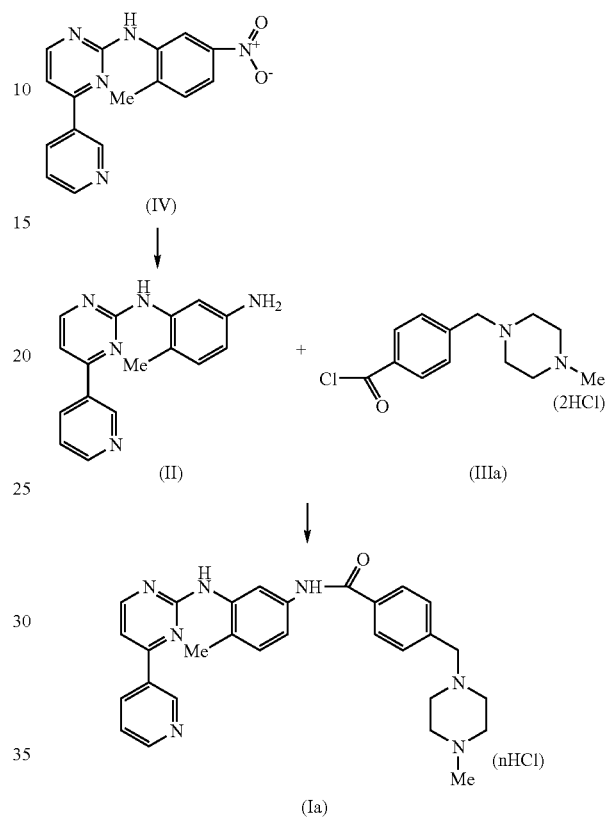

wherein the reduction of (2-methyl-5-nitrophenyl)-6-pyridin-3-yl-1,6-dihydro-pyrimidine-2-yl)-amine of formula (IV) to yield N-(2-methyl-5-aminophenyl-4-(3-pyridyl)-2-pyrimidine amine of formula (II) is carried out in the presence of a chemical reducing agent and the reaction of N-(2-methyl-5-aminophenyl-4-(3-pyridyl)-2-pyrimidine amine of formula (II) with 4-(4-methyl-piperazino methyl)benzoyl chloride of formula (IIIa) is carried out in the presence of an inert organic solvent, so as to yield a hydrochloride salt of imatinib of formula (Ia) where n represents 1, 2 or 3 either in anhydrous or hydrated form, which can as desired optionally be further converted either to the free base or a further acid addition salt.

* * * * *

UNITED STATES PATENT AND TRADEMARK OFFICE
CERTIFICATE OF CORRECTION

PATENT NO.       : 7,638,627 B2
APPLICATION NO.  : 10/546193
DATED            : December 29, 2009
INVENTOR(S)      : Rajendra Narayanrao Kankan and Dharmaraj Ramachandra Rao It is certified that error appears in the above-identified patent and that said Letters Patent is hereby corrected as shown below:

Column 13, Line 53 Claim 12, replace "with a methyl-" with -- with a 4-(4-methyl- --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,638,627 B2
APPLICATION NO. : 10/546193
DATED : December 29, 2009
INVENTOR(S) : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 924 days.

Signed and Sealed this

Ninth Day of November, 2010

David J. Kappos
*Director of the United States Patent and Trademark Office*